United States Patent [19]
Tsaur

[11] Patent Number: 6,126,954
[45] Date of Patent: Oct. 3, 2000

[54] LIQUID COMPOSITIONS COMPRISING STABLE EMULSION OF SMALL PARTICLE SKIN BENEFIT AGENT

[75] Inventor: Liang Sheng Tsaur, Norwood, N.J.

[73] Assignee: Unilever Home & Personal Care USA, division of Conopco, Greenwich, Conn.

[21] Appl. No.: 09/286,041

[22] Filed: Apr. 5, 1999

[51] Int. Cl.⁷ .................................. A61K 7/48; A61K 7/50
[52] U.S. Cl. ................... 424/401; 424/70.11; 424/70.13; 424/70.21; 424/70.22; 424/70.31; 424/78.03; 510/121; 510/475; 514/846
[58] Field of Search ................ 424/70.11, 70.13, 424/70.21, 70.22, 70.31, 78.02, 78.03, 401; 510/119, 121, 123, 129, 130, 159, 405, 475; 514/846

[56] References Cited

U.S. PATENT DOCUMENTS

| | | |
|---|---|---|
| 3,580,853 | 5/1971 | Parran, Jr. . |
| 5,085,857 | 2/1992 | Reid et al. . |
| 5,308,526 | 5/1994 | Dias et al. . |
| 5,439,682 | 8/1995 | Wivell et al. . |
| 5,518,647 | 5/1996 | Zocchi . |
| 5,543,074 | 8/1996 | Hague et al. ............................. 510/122 |
| 5,661,189 | 8/1997 | Grieveson et al. ...................... 514/784 |
| 5,783,536 | 7/1998 | Farrell et al. ........................... 510/141 |
| 5,858,939 | 1/1999 | Tsaur ....................................... 510/141 |
| 5,900,394 | 5/1999 | Goel et al. .............................. 510/141 |
| 5,912,002 | 6/1999 | Grieveson et al. ...................... 424/401 |

FOREIGN PATENT DOCUMENTS

| | | |
|---|---|---|
| 92/18100 | 10/1992 | WIPO . |
| 94/03152 | 2/1994 | WIPO . |
| 96/02225 | 1/1996 | WIPO . |
| 96/17592 | 6/1996 | WIPO . |
| 97/48378 | 12/1997 | WIPO . |

*Primary Examiner*—Robert H. Harrison
*Attorney, Agent, or Firm*—Ronald A. Koatz

[57] ABSTRACT

A stable aqueous liquid comprising surfactant, dispersed cationic polymer particle and small particle benefit agent. The dispersed polymer interacts with the benefit agent, without need of additional structurant to stabilize particles in solution. Further, upon dilution, enhanced cationic deposition is achieved.

14 Claims, No Drawings

LIQUID COMPOSITIONS COMPRISING STABLE EMULSION OF SMALL PARTICLE SKIN BENEFIT AGENT

FIELD OF THE INVENTION

The present invention relates to stable aqueous liquid cleansing compositions comprising small droplets of skin benefit agents and dispersed cationic polymer particles. In particular, the invention relates to aqueous liquid compositions in which small particle benefit agents are stably suspended and readily deposited upon dilution with water. Stability is accomplished through interaction of said small particle benefit agents and dispersed cationic polymers in said composition to form a microscopically visible, stable, benefit agent/polymer network. Upon dilution of said liquid compositions in water, the dispersed cationic polymers dissolve rapidly and interact with the small particles of benefit agent to achieve high deposition of skin benefit agent.

BACKGROUND OF THE INVENTION

In addition to cleaning, another highly desirable characteristic of personal cleanser/shower gel type compositions is to deliver consumer perceivable skin benefits from the compositions to the skin. One important way of achieving this result is through high deposition of emollient oils. In turn, this requires incorporation of high levels of oil into the cleanser/shower gel composition.

Unfortunately, dual cleansing and moisturizing compositions are difficult to formulate because cleansing ingredients, in general, tend to be incompatible with moisturizing ingredients. For example, emulsified oil droplets, especially hydrocarbon oil droplets, tend to phase separate from liquids during storage and form a separate layer at the top of the liquid cleanser. Furthermore, without an efficient deposition mechanism, oil droplets contained in the cleansing composition can be washed off from the skin by surfactants during the use of the product preventing the high deposition needed for perceivable skin benefit.

Another problem is that emollient oils often tend to depress foaming/lathering of cleansing ingredients. Further the best foaming cleansing surfactants also tend to be the least mild (i.e., they are irritating to the skin).

Accordingly, there is a need in the art for a composition which contains cleansing ingredients (which are both mild and capable of producing abundant lather) and which also can deliver moisturizing ingredients while remaining physically stable.

Liquid cleansers which can deliver skin benefit agents to provide some kind of skin benefit are known in the art. For example, one method of enhancing delivery of benefit agent to the skin or hair is using prehydrated cationic polymers such as Polymer JR® from Amerchol or Jaguar® from Rhone Poulenc. This method is disclosed, for example, in U.S. Pat. No. 3,580,853 to Parran et al, U.S. Pat. No. 5,085,857 to Reid et al., U.S. Pat. No. 5,439,682 to Wivell et al; or in WO 94/03152 (assigned to Unilever), WO 92/18100 (assigned to Procter & Gamble) or WO 97/48378 (assigned to Procter & Gamble).

In the patents noted above, to achieve oil deposition or skin conditioning effect the cationic polymers are premixed with an aqueous solution either with or without the presence of skin benefit agents to hydrate and dissolve the polymer before mixing with cleansing agents. Since they are dissolved, the cationic polymers are not visible even under a microscope. Dissolution of these cationic polymers in water is time consuming and costly, and can cause problems in processing, especially when a high level of cationic polymer is used in the composition in order to get high deposition of skin benefit agents. It is also known that liquid cleansing products containing high level of pre-dissolved cationic polymer is not desirable due to lower lather speed and slimy feel. Processing difficulties and undesirable in-use properties tend to prevent the use of high level of cationic polymer in the liquid cleanser to achieve high deposition of oils on to the skin.

Further, the art teaches that physical stability of the emollient oil cleanser system requires the presence of some sort of suspending or stabilizing agent other than cationic. U.S. Pat. No. 5,308,526 to Dias et al and U.S. Pat. No. 5,439,682 to Wivell et al, for example, teach the use of crystalline ethylene glycol long chain esters (e.g., ethylene glycol distearate) as suspension agent to prevent separation of oil droplets from the liquid. U.S. Pat. No. 5,518,647 to Zocchi teaches an emulsion system combining long chain ethoxylated alcohol, free fatty carboxylic acid and water soluble polymer to achieve physical stability of oil droplets in liquid cleanser. Another type of well-known suspension agents used to stabilize oil droplets in liquid cleansers are high molecular weight water-soluble polymers such as polyacrylate, modified celluloses and guar polymers as disclosed, for example, in WO 96/02225 (assigned to Unilever). Although these materials are effective for suspending oil droplets, they are expensive ingredients and, as is the case with cationic polymers, at higher levels they tend to cause difficulty in processing and to impart an undesirable slimy feel during the use of the product.

Without imparting negative effects on important cleanser properties (such as lather and in-use sensory properties) and its processability, applicants have found that storage stable liquid cleansers containing high level of oils (e.g., 1 to 30%, preferably 3 to 30% by wt.) and high level of cationic polymer (0.1 to 5%, preferably 0.3 to 5% by wt.) can be formulated using cleanser insoluble, water soluble cationic polymer particles as the stabilizer. In this invention, cleanser stability is achieved by structuring the liquid with particles of skin benefit agents themselves without the need for conventional thickeners.

BRIEF DESCRIPTION OF THE INVENTION

The present invention relates to a composition comprising stable moisturizing liquid cleansers containing high level of emollient oils (up to 30%); humectants; and dispersed cationic particles and to a process to prepare such liquids. Formulating liquids containing high level of hydrocarbon oils is known to be difficult due to rapid separation of oils. In this invention, stability is achieved by structuring the liquids using particles of skin benefit agents themselves (interacting with cationic polymer). Moreover, there is no need for conventional thickeners. As noted, solid cationic polymer (0.1, preferably 0.3 to 5 wt. %) is added to and exists in the liquid as dispersed particles to structure the oils in the liquids. Since no pre-hydration of cationic is needed in the process, a high level of polymer can be formulated in the liquid cleanser without imparting any process difficulty and undesirable in-use properties. This is important for achieving higher deposition of polymer when liquids are later diluted.

As noted liquid stability is achieved through the interaction of dispersed cationic polymer particles (1 to 100 micrometers) and the small oil droplets (said oil droplets having a particle size in the range of 0.1 to 10 micrometers). Upon dilution of the liquid composition with water, the dispersed cationic particles dissolve rapidly and interact with the small oil droplet to form large oil aggregates with a length larger than 50 micrometers. Enhanced deposition of the oil droplets onto the skin is achieved due to aggregate formation induced by the added cationic polymers. Liquid cleansers structured with this novel structuring system are stable at elevated temperature and provide good cleansing and skin conditioning properties (by stable is meant there was no phase separation at 40° for at least 1 week or at room temperature for at least one month). High level of cationic guar polymer can be formulated into the liquid to achieve high deposition for skin benefits without causing either undesirable in-use sensory properties or processing problems.

More specifically, the compositions of the invention comprise:

(a) 5 to 45%, preferably 5 to 35% by wt. surfactants selected from the group consisting of anionic surfactant, amphoteric surfactant, nonionic surfactant and mixtures thereof;

(b) 0.1 to 5.0%, preferably 0.3 to 5% by wt. dispersed particles of cationic polymer having a particle size of about 1 to about 200 micrometers, preferably about 2 to 100 micrometers;

(c) 1 to 30%, preferably 3 to 25% by wt. of a skin benefit agent emulsion having a particles size in the range of about 0.1 to about 10 micrometers, preferably 0.1 to 5 micrometers; and (d) 1 to 30 wt %, preferably 3 to 20% by wt. of water soluble skin benefit agents wherein, upon dilution of the liquid composition with water, said dispersed cationic polymer dissolves and interacts with said skin benefit agent emulsion to form emulsion/polymer aggregates having a length larger than about 50 micrometers. These aggregates provide enhanced benefit agent deposition.

DETAILED DESCRIPTION OF THE INVENTION

The present invention relates to stable aqueous liquid cleanser compositions comprising skin benefit agent emulsions and dispersed cationic polymer particles. The compositions may contain large amounts of cationic (since they are dispersed and not prehydrated), are stable and can deliver larger amounts of both benefit agent and cationic polymer. The dispersed cationic particles can be distinguished from prehydrated cationic in that they are visible as particles under a microscope while prehydrated cationic is not visible.

It is very difficult to make mild cleansing compositions which foam well, contain benefit agent emulsions and which are physically stable, particularly in the absence of stabilizers or suspending agents. It is further difficult to get high deposition of benefit agent from liquids.

Unexpectedly, applicants have found that it is possible to make cleaning compositions comprising stable skin benefit agent emulsions by actually stabilizing the skin benefit agents (of relatively small size) with dispersed cationic polymer particles. While not wishing to be bound by theory, it is believed that small size benefit agent emollient (i.e., about 0.1 to 10 micrometers) is stabilized in the cleansing composition due to its interaction with dispersed water-soluble cationic polymer particle to form a network stable in the solution (this network is separate from the "aggregates" formed between benefit agent and polymer discussed below). Moreover, since this cationic need not be pre-dissolved, much more of it can be used than is normally the case, thereby allowing higher deposition upon dilution.

Further, applicants have found that, upon dilution with water, the benefit agent emollient/oil and polymer interact to form aggregates, larger than about 50 micrometers, which readily deposit on skin or other substrate (plus, as noted, there is more cationic to begin with).

More specifically, the application is set forth in greater detail below:

Surfactant

The surface active agent can be selected from any known surfactant suitable for topical application to the human body. Mild surfactants, i.e., surfactants which do not damage the stratum corneum, the outer layer of skin, are particularly preferred.

One preferred anionic detergent is fatty acyl isethionate of formula:

$$RCO_2CH_2CH_2SO_3M$$

where R is an alkyl or alkenyl group of 7 to 21 carbon atoms and M is a solubilizing cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

$$RO(CH_2CH_2O)_n SO_3M$$

where R is an alkyl group of 8 to 22 carbon atoms, n ranges from 0.5 to 10 especially from 1.5 to 8, and M is a solubilizing cation as before.

Other possible anionic detergents include alkyl glyceryl ether sulphate, sulphosuccinates, taurates, sarcosinates, sulphoacetates, alkyl phosphate, alkyl phosphate esters and acyl lactylate, alkyl glutamates and mixtures thereof.

Sulphosuccinates may be monoalkyl sulphosuccinates having the formula:

$$R^5O_2CCH_2CH(SO_3M)CO_2M;$$

and amido-MEA sulphosuccinates of the formula:

$$R^5CONHCH_2CH_2O_2CCH_2CH(SO_3M)CO_2M;$$

wherein $R^5$ ranges from $C_8$–$C_{20}$ alkyl, preferably $C_{12}$–$C_{15}$ alkyl and M is a solubilizing cation.

Sarcosinates are generally indicated by the formula:

$$R^5CON(CH_3)CH_2CO_2M,$$

wherein $R^5$ ranges form $C_8$–$C_{20}$ alkyl, preferably $C_{12}$–$C_{15}$ alkyl and M is a solubilizing cation.

Taurates are generally identified by the formula:

$$R^5CONR^6CH_2CH_2SO_3M,$$

wherein $R^5$ ranges from $C_8$–$C_{20}$ alkyl preferably $C_{12}$–$C_{15}$ alkyl, $R^6$ ranges from $C_1$–$C_4$, and M is a solubilizing cation.

Harsh surfactants such as primary alkane sulphonate or alkyl benzene sulphonate will generally be avoided.

Suitable nonionic surface active agents include alkyl polysaccharides, lactobionamides, ethylene glycol esters, glycerol monoethers, polyhydroxyamides (glucamade), primary and secondary alcohol ethoxylates, especially the $C_8$–$C_{20}$ aliphatic alcohols ethoxylated with an average of from 1 to 20 moles of ethylene oxide per mole of alcohol.

If the surface active agent comprises soap, the soap is preferably derived from materials with a $C_8$ to $C_{22}$ substantially saturated carbon chain and, preferably, is a potassium soap with a $C_{12}$ to $C_{18}$ carbon chain.

Mixtures of any of the foregoing surface active agents may also be used.

The surface active agent is preferably present at a level of from 5 to 35 wt. %, more preferably 10 to 30 wt. %.

It is also preferably that the composition includes from 3 to 15 wt. % of a cosurfactant agent with skin-mildness benefits. Suitable materials are zwitterionic detergents which have an alkyl or alkenyl group of 7 to 18 carbon atoms and comply with an overall structural formula:

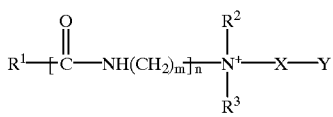

where
$R^1$ is alkyl or alkenyl of 7 to 18 carbon atoms $R_2$ and $R_3$ are each independently alkyl, hydroxyalkyl or carboxyalkyl of 1 to 3 carbon atoms;
m is 2 to 4;
n is 0 or 1;
X is alkylene of 1 to 3 carbon atoms optionally substituted with hydroxyl; and
Y is $-CO_2$ or $-SO_3$.

Zwitterionic detergents within the above general formula include simple betaines of formula:

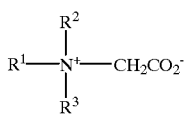

and amido betaines of formula:

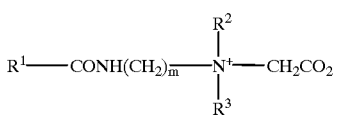

where m is 2 or 3.

In both formulae $R^1$, $R^2$ and $R^3$ are as defined previously. $R^1$ may, in particular, be a mixture of $C^{12}$ and $C^{14}$ alkyl groups derived form coconut so tat at least half, preferably at least three quarters, of the group $R^1$ has 10 to 14 carbon atoms. $R^2$ and $R^3$ are preferably methyl.

A further possibility is a sulphobetaine of formula:

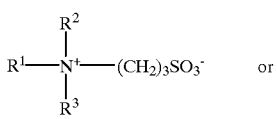 or

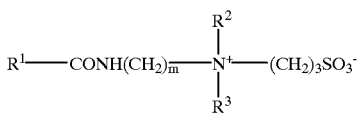

where m is 2 or 3, or variants of these in which $-(CH_2)_3SO_3-$ is replaced by:

$R^1$, $R^2$ and $R^3$ in these formulae are as defined previously.

In general, total surfactants is generally used at about 5% to 45% of the compositions, preferably 5 to 35%.

Cationic Polymer

In a second requirement of the invention, the invention comprises 0.1 to 5.0%, preferably 0.3 to 5%, more preferably 1% to 5% by wt. dispersed cationic polymer particles which both stabilize the skin benefit agents in the liquid cleanser (by forming a network between the emollient and dispersed cationic) and also works as deposition aid to deposit the skin benefit agents onto the skin during the use of the liquid cleanser (by forming aggregates between benefit agent and polymer) The cationic may be a "standard" cationic polymer or an amphoteric polymer containing both cationic and anionic group with net cationic charge.

The cationic polymer exists in the liquid cleanser as dispersed particles with particle size in the range of 1 to 200 micrometers, preferably 2 to 100 micrometers. These dispersed cationic polymer particles (by "dispersed" is meant that the particles can be seen as particles under the microscope) dissolve rapidly upon dilution of the liquid cleanser with water to induce aggregations of skin benefit agents (i.e., benefit agent plus cationic polymer aggregates) and achieve high deposition onto the skin.

Cationic polymers suitable for this invention should be solid water-soluble polymer particles which are insoluble in the cleanser. As noted, prehydrating or pre-dissolving the solid polymer particle in an aqueous solution before mixing it with the surfactant solution is unnecessary and not preferred. The cationic polymer is generally added into the liquid cleanser as a pre-dispersion. The polymer pre-dispersion is prepared by mixing the solid polymer with water mixable ingredients such as glycerol or propylene glycol. It can also be prepared by mixing the particles with low viscosity oils such as mineral oil, perfume or by mixing the polymer particle with an aqueous solution under such conditions that the polymer particles will not dissolve (for example, dispersing Jaguar C13S powder in an alkaline aqueous solution). Polymer pre-dispersion prepared by mixing with either water-soluble ingredients or with an aqueous solution is preferred. The pre-dispersion is preferred to have a viscosity less than 100,000 centipoise, more preferably less than 10,000 centipoise, most preferable less than 1,000 centipoise. Thus it can be processed and mixed easily with the liquid cleanser.

Examples of cationic polymers suitable for the present invention are modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance 3000, N-Hance 3196, N-Hance GPX 215 or N-Hance GPX 196 from Hercules; cationic starches, e.g., StaLok(®) 100, 200, 300 and 400 made by Staley Inc.; and cationic galactomannans based on guar gum of Galactasol 800 series by Henkel, Inc.

As noted below, and without wishing to be bound by theory, it is believed that it is "network" formed from interaction of the dispersed polymer particles and emulsion of benefits agents which are key to the invention for the physical stability of the liquid composition. Dispersed cationic polymer particle alone, as shown in Example 1, might not be physically stable by themselves in the liquid cleanser.

Without small oil droplet emulsion, these polymer particles precipitate to the bottom of the liquid composition during storage. With the addition of small oil droplet emulsion, the dispersed cationic particles interact with the oil droplet to form a stable network so that they will not precipitate out of solution even without the aid of additional structurant. The dispersed cationics, when later diluted in use, interact with benefit agent to form aggregates which enhance deposition.

Benefit Agent/Oil Droplet

The benefit agent is included in the composition to moisturize, condition and/or protect the skin. By "benefit agent" is meant a substance that softens the skin (stratum corneum) and keeps it soft by retarding the decrease of its water content and/or protects the skin.

Preferred benefit agents include:

a) silicone oils, gums and modifications thereof such as linear and cyclic polydimethylsiloxanes, amino, alkyl alkylaryl and aryl silicone oils;

b) fats and oils including natural fats and oils such as jojoba, soybean, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride;

c) waxes such as carnauba, spermaceti, beeswax, lanolin and derivatives thereof;

d) hydrophobic plant extracts;

e) hydrocarbons such as liquid paraffins, petroleum jelly, microcrystalline wax, ceresin, squalene, and mineral oil;

f) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate for example lauryl lactate, alkyl citrate and alkyl tartrate;

g) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;

h) lipids such as cholesterol, ceramides, sucrose esters and pseudo-ceramides as described in European Patent Specification No. 556,957;

i) vitamins such as A and E, and vitamin alkyl esters, including those vitamin C alkyl esters;

j) sunscreens such as octyl methoxyl cinnamate (Parsol MCX) and butyl methoxy benzoylmethane (Parsol 1789);

k) Phospholipids; and l) mixtures of any of the foregoing components.

Where adverse interactions between the benefit agent and surface active are likely to be particularly acute, the benefit agent may be incorporated in the compositions of the invention in a carrier.

Such benefit agents include lipids; alkyl lactates; esters such as isopropyl palmitate and isopropyl myristate; sunscreens; and vitamins. The carrier can, for example, be a silicone or hydrocarbon oil which is not solubilized/micellized by the surface active phase and in which the benefit agent is relatively soluble.

Particularly preferred benefit agents include petrolatum, silicone oils, triglyceride oils and modification thereof; esters such as isopropyl palmitate and myristate and alkyl lactates.

The benefit agent is preferably present in amount of from 1 to 30 wt. %, preferably from 3 to 25 wt. %.

The benefit agent droplets/emulsion of the invention have a particle size in the range of about 0.1 to 10 micrometers, preferably 0.1 to 5 micrometers.

While not wishing to be bound by theory, it is believed the dispersed cationic polymer particle interacts with skin benefit agent to form emulsion/polymer network. Stability of small droplet emulsion and dispersed polymer particle is achieved due to the formation of these emulsion/polymer networks.

By structuring benefit agent with cationic polymers, use of any other structurant can be minimized or avoided altogether.

Water Soluble Benefit Agents

Another essential ingredient that is preferred to be included in the liquid composition is water-soluble skin benefit agent. A variety of water-soluble skin benefit agents can be used and the level can be from 1 to 30 weight %, preferably 1 to 20% by wt. Skin conditioning effect of deposited oils can be enhanced by addition of these water-soluble skin benefit agents. The water soluble benefit agent, as described above, can also work as processing aid for the addition of solid cationic polymer particles. The materials include, but are not limited to, polyhydroxy alcohols such as glycerol, propylene glycol, sorbitol, pantenol and sugar; urea, alpha-hydroxy acid and its salt such as glycolic or lactic acid; and low molecular weight polyethylene glycols with molecular weight less than 20,000. Preferred water soluble skin benefit agents for use in the liquid composition are glycerol, sorbitol and propylene glycol In a second embodiment of the invention, the invention relates to a process for enhancing deposition of small particle oil/emollient droplets (0.1 to 10 micrometers, preferably 0.1 to 5 micrometers, more preferably 0.1 to 3 micrometers) by first combining oil droplets with cationic polymers as discussed above in an aqueous surfactant solution and subsequently diluting the compositions upon use in water. Upon dilution with water, the dispersed cationic polymer particle dissolves and induces "aggregates" of small oil droplets having particle size with length greater than 50 micrometers. These aggregates are different from the networks formed before dilution The present invention is set forth in greater detail in the examples that follow. The examples are for illustration purposes only and are not intended to be limiting in any way.

All percentages in the examples and specification, unless indicated otherwise, are intended to be percentages by weight.

All numerical values and ranges in the specification are intended to be modified by the word "about".

Finally, the term comprising, where used in the specification or claims, is intended to specify the presence of stated features, integers, steps, components, but not to preclude the presence of addition of one or more features, integers, steps, components or groups thereof.

EXAMPLES

Example 1

The following example shows that dispersed cationic guar particles alone can work as an effective stabilizer for oil droplets in surfactant solution. Without the need of other structuring agents, stable moisturizing liquid can be prepared using combination of dispersed cationic guar particles and small droplet emulsion of skin benefit agents. Three samples with compositions shown in the table below were prepared. Example 1 is an example of this invention. Examples A and B were prepared for comparison. All the surfactants, NaOH solution and deionized water were added to a conventional mixer and mixed at 70° C. to 75° C. for about 30 minutes to form an uniform solution. Silicone emulsion and sunflower oil emulsion were then added to the surfactant solution and mixed at 55° C. to 60° C. for about 10 to 20 minutes. Jaguar C13S was mixed with glycerine to form guar powder dispersion. The dispersion was then added into the mixer and mixed for 20 to 30 minutes. The mixer was then cooled to around 35° C. Perfume and glydant plus were added and mixed for about 20 minutes. The prepared liquids were cooled and discharged from the mixer.

Stability of these three liquids was compared by storing the samples in 40° C. oven for one week. The result was also shown in the table below. Example 1, an example of this invention containing both oil emulsions and dispersed cationic guar particles, was stable after storage. Comparative Examples A and B, containing either the dispersed guar particle or the oil emulsions alone, were not stable. A creamy layer of oils floated to the top for Comparative A and a layer of polymer gel particles precipitated at the bottom of Comparative B.

|  | Example 1 | Comparative A | Comparative B |
|---|---|---|---|
| Na Cocamidopropyl Betaine | 8.0 | 8.0 | 8.0 |
| Na Laureth (3) Sulfate | 2.0 | 2.0 | 2.0 |
| Na Cocoisethionate | 5.0 | 5.0 | 5.0 |
| Silicone oil emulsion (50%) | 15 | 15 | 0.0 |
| Sunflower oil emulsion (50%) | 15 | 15 | 0.0 |
| NaOH (50%) | 0.1 | 0.1 | 0.1 |
| Cationic guar (Jaguar C13S) | 1.2 | 0.0 | 1.2 |
| Glycerine | 5.0 | 5.0 | 5.0 |
| Glydant Plus | 0.2 | 0.2 | 0.2 |
| Perfume | 1.0 | 1.0 | 1.0 |
| Water | To 100 wt. % | To 100 wt. % | To 100 wt. % |
| Stability (1 week storage at 40° C.) | | | |
| | Stable | Phase separate Cream to the top | Phase separate Precipitate |

Example 2

Another comparative example with a composition same as example 1 is prepared to show the advantage of this invention over the preferred method taught in the prior art. Instead of adding the cationic guar as dispersed particles into the surfactant mixture (as per subject invention), the cationic guar was first prehydrated in aqueous solution before being mixed with the surfactant mixture (as is taught in the prior art). All the surfactants (Cocamidopropyl betaine, laureth sulfate and cocoisethionate), NaOH and calculated amount of water were mixed at 70° C. to 75° C. to form surfactant premix with % solid equal to 30% solid. Jaguar C13S was mixed with the remaining water, silicone emulsion, sunflower oil emulsion and glycerol in the mixer at 70° C. for about 30 minutes to prehydrate the cationic guar. Surfactant premix was then added into the reactor and mixed for about 30 minutes at 60° C. The reactor was cooled to 35° C. Perfume and glydant plus were added. It was noticed that there were polymer gels coated on the stirrer and large lumps of polymer gels contained in the prepared liquid. The liquid was not stable and showed phase separation after being stored at 40° C. for 1 week.

This example demonstrates that the procedure of this invention (using dispersed particles rather than prehydrating) provides a better way to process liquid containing high level of cationic guar polymers. It also shows that better stability was achieved using the suspended guar particle as emulsion stabilizer instead of using fully hydrated cationic guar polymers which are preferred in the prior art.

Examples 3–4

Deposition of Skin Benefit Agent

This example shows that high deposition of skin benefit agent can be achieved without prehydrating the cationic polymer before mixing it with a surfactant solution. Deposition efficiency depends on the dissolution of the suspended cationic guar particles upon dilution of the liquid with water. To achieve high deposition, the suspended cationic guar particles have to dissolve rapidly during use of the liquids to interact with and to deposit the oil emulsions onto the skin.

|  | Example 3 | Example 4 | Comparative C |
|---|---|---|---|
| Na Cocamidopropyl Betaine | 10.0 | 10.0 | 10.0 |
| Na Laureth (3) Sulfate | 2.0 | 2.0 | 2.0 |
| Na Cocoisethionate | 3.0 | 3.0 | 3.0 |
| Silicone oil emulsion (50%) | 20 | 20.0 | 20.0 |
| NaOH (50%) | 0.1 | 0.1 | 0.1 |
| (Jaguar C13S)* | 0.6 | — | — |
| Miracare XC96/21** | — | 0.6 | — |
| Miracare XC 96/25** | — | — | 0.6 |
| Glycerine | 2.0 | 2.0 | 2.0 |
| Antil 141*** | 1.0 | 1.0 | 1.0 |
| Glydant Plus | 0.2 | 0.2 | 0.2 |
| Perfume | 1.0 | 1.0 | 1.0 |
| Water | To 100 wt. % | To 100 wt. % | To 100 wt. % |
| Stability (1 week storage at 40° C.) | | | |
| | Stable | Stable | Stable |

*Cationic guar from Rhone-Poulenc
**Amphoteric guar from Rhone-Poulenc with net cationic charge
***Polyethylene propylene glycol oleate All the above three samples contain dispersed guar particles as observed under optical microscope. Upon dilution of the liquid with water, the dispersed guar particles dissolve rapidly for both Examples 3 and 4. For comparative C, most of the guar particles remain intact after diluting the liquid with water. Deposition of the above three samples on adult porcine skin purchased from Buckshire was measured using the following method.

Porcine skin of 3×3 square inches was prewetted with tap water. 0.52 grams of the liquid was placed and rubbed on the skin for 15 seconds. The skin was then rinsed under tap water at a flow rate about 13 cc per minute for 15 seconds. After rinsing the skin was patted dry with paper towel once and air dried for 2 minutes. The deposited silicone oil was then extracted with known amount of xylene. The silicone content in the xylene extract was analyzed using inductively coupled argon plasma atomic emission technique (Thermo Jarrell Ash AtomScan-25 inductively coupled plasma spectrophotometer). Deposition of these three samples is summarized in the following table. It clearly shows that liquids (Examples 3 & 4) containing the composition as described in this invention deposit significantly higher amount of skin benefit agents than Comparative C which do not contain the type of cationic solid polymer suitable for the use of this invention.

|  | Example 3 | Example 4 | Comparative C |
|---|---|---|---|
| Silicone Deposition (micrograms/cm$^2$) | 41.5 | 43.5 | 3.82 |

Example 5
Effect of Cationic Guar Level on Stability

|  | Comparative D | Example 5 | Example 6 |
|---|---|---|---|
| Na Cocamidopropyl Betaine | 10 | 10 | 7.0 |
| Na Laureth (3) Sulfate | 2.0 | 2.0 | 3.5 |
| Na Cocoisethionate | 3.0 | 3.0 | 4.5 |
| Silicone oil emulsion (50%) | 15 | 15 | 15 |
| Sunflower oil emulsion (50%) | 15 | 15 | 15 |
| NaOH (50%) | 0.1 | 0.1 | 0.1 |
| Cationic guar (Jaguar C13S) | 0.7 | 2.0 | 0.7 |
| Glycerine | 3.5 | 6.0 | 3.5 |
| Glydant Plus (Preservative) | 0.2 | 0.2 | 0.2 |
| Antil 141 | 1.0 | 0.0 | 0.0 |
| Perfume | 1.0 | 1.0 | 1.0 |
| Water | To 100 wt. % | To 100 wt. % | To 100 wt. % |
| Stability at 40° C. for 1 week |  |  |  |
|  | Not stable | Stable | Stable |

The above liquids were prepared using the same procedure described in Example 1. These samples contained different surfactant mixture and different level of cationic guar dispersion. Comparative D was not stable after storage. Examples 5 and 6 were stable at 40° C. This example shows that stability of liquids depends on the surfactant composition and the level of cationic polymer used in the composition. For example, it can be seen that 0.7 cationic was sufficient to stabilize composition 6 containing only 7.0% betaine but did not stabilize composition D containing 10% betaine. Addition of more cationic (Example 5) or decreasing betaine (Example 6) helped stabilize the compositions.

Examples 7–9 and Comparatives E and F

|  | Example 7 | Example 8 | Example 9 | Comparative E | Comparative F |
|---|---|---|---|---|---|
| Na Cocamidopropyl Betaine | 10 | 10 | 10 | 10 | 10 |
| Na Laureth (3) Sulfate | 2.0 | 2.0 | 2.0 | 2.0 | 2.0 |
| Na Cocoisethionate | 3.0 | 3.0 | 3.0 | 3.0 | 3.0 |
| Silicone oil emulsion (50%) | 15 | 15 | 15 | 15 | 15 |
| Sunflower oil emulsion (50%) | 15 | 15 | 15 | 15 | 15 |
| NaOH (50%) | 0.1 | 0.1 | 0.1 | 0.1 | 0.1 |
| Cationic guar (Jaguar C13S) | 2.0 | — | — | — | — |
| Cationic guar (Polymer JR) | — | 2.0 | — | — | — |
| Cationic guar (N-Hance 3215) | — | — | 2.0 | — | — |
| Merquart 100 | — | — | — | 2.0 | — |
| Merquart 550 | — | — | — | — | 2.0 |
| Glycenne | 2.5 | 2.5 | 6.0 | 3.5 | 3.5 |
| Glydant Plus | 0.2 | 0.2 | 0.2 | 0.2 | 0.2 |
| Antil 141 | 1.0 | 1.0 | 0.0 | 0.0 | 0.0 |
| Perfume | 1.0 | 1.0 | 1.0 | 1.0 | 1.0 |
| Water | To 100 wt. % | To 100 wt. % | To 100 wt. % | To 100 wt. % | To 100 wt. % |

The example above shows effect of cationic polymer type on liquid stability. Jaguar C13S, Polymer JR and N-Hance are solid cationic guar polymers (stability obtained) and Merquart 100 and Merquart 550 are presolubilized aqueous polymer solution (no stability obtained).

The above liquids were prepared using the same procedure described in Example 1 except Comparatives E and F in which the cationic polymer, i.e., Merquart 100 and Merquart 550, were added without premix with glycerol. Glycerol for Comparative Example E and F were added after adding the cationic polymer. Examples 7, 8 and 9 were stable at 40° C. for 1 week. Comparative Samples E and F were not stable with a clear layer formed at the bottom of the samples.

Examples 10–13

These examples show that this invention is suitable for a variety of oils and surfactant mixture. All the samples prepared according to the method described in Example 1 were stable after 1 week, 40° C. storage.

|  | Example 10 | Example 11 | Example 12 | Example 13 |
|---|---|---|---|---|
| Na Cocamidopropyl Betaine | 7 | 5 | 5 | 10 |
| Na Laureth (3) Sulfate | 3.5 | — | — | 5 |
| Na Cocoisethionate | 4.5 | — | — | 0 |
| Lauryl Polyglucoside | — | 3 | — | — |
| Na Laurylamphoacetate | — | 7 | — | — |
| Cocoamido 3EO sulfate | — | — | 10 | — |
| Petrolatum emulsion (50%) | 34 | 44 | 24 | — |
| Silicone oil emulsion (50%) | 6 | 6 | 6 | — |
| Sunscreen/sunflower oil emulsion* (50%) | — | — | — | 30 |
| Cationic guar (Jaguar C13S) | 1.5 | 2.0 | 1.6 | 1.8 |
| Glycerine | 5.0 | 6.0 | 5.0 | 6.0 |
| Glydant Plus | 0.2 | 0.2 | 0.2 | 0.2 |
| Perfume | 1.0 | 1.0 | 1.0 | 1.0 |
| Water | To 100 wt. % | To 100 wt. % | To 100 wt. % | To 100 wt. % |

*The emulsion contains 20% Parsol MCX (sunscreen) and 80% of sunflower oil which was prepared by homogenized 50 wt. % of Parsol MCX and sunflower oil mixture in 50 wt. % of aqueous solution containing 3 wt. % of sodium cocamidopropylbetaine and 2 wt. % of sodium laureth sulfate.

I claim:
1. An aqueous liquid composition comprising:
 (a) 5 to 45% by wt. of a surfactant selected from the group consisting of anionic surfactant, amphoteric surfactant, nonionic surfactant and mixtures thereof;

(b) 0.1 to 5.0% by wt. dispersed cationic polymer particles having a particle size of about 1 to about 200 micrometers;

(c) 1 to 30% by wt. of a skin benefit agent emulsion having a particles size in the range of about 0.1 to about 10 micrometers;

(d) 1 to 30% by wt. of water soluble skin benefit agent; wherein upon dilution of the liquid composition with water, said dispersed cationic polymer particle (b) dissolves and interacts with said skin benefit agent emulsion (c) to form emulsion/polymer aggregates having a length larger than about 50 micrometers.

2. A composition according to claim 1 comprising 5 to 35% by wt. surfactant.

3. A composition according to claim 1, wherein cationic polymer is an amphoteric polymer containing a cationic and anionic group wherein the polymer has a net cationic charge.

4. A composition according to claim 1, wherein cationic polymer is added to the composition as a pre-dispersion prepared by mixing a solid cationic polymer with water soluble ingredients; with low viscosity oils; or with aqueous solution under such conditions that the polymer particles will not dissolve.

5. A composition according to claim 4, wherein said pre-dispersion has a viscosity of less than 100,000 centipoise.

6. A composition according to claim 1, wherein cationic polymer has particle size of 1 to 100 micrometer.

7. A composition according to claim 1, wherein the skin benefit agent from emulsion (c) has particle size of 0.1 to 5 micrometers.

8. A composition according to claim 1 containing 0.3 to 5% by wt. cationic polymer.

9. A composition according to claim 1, where benefit agent emulsion (c) comprises 3 to 25% by wt. of composition.

10. A composition according to claim 1, comprising substantially no structurants.

11. A composition according to claim 1, wherein said water soluble benefit agent (d) is a polyhydroxy alcohol.

12. A composition according to claim 11, wherein said alcohol is selected from the group consisting of glycerol, sorbitol and polyalkylene glycol.

13. A composition according to claim 1 comprising 3 to 20% by wt water soluble skin benefit agent.

14. A process for enhancing deposition of oil/emollient droplets having a particle size of 0.1 to 10 micrometers which process comprises:

(a) combining said oil droplets with dispersed cationic polymer in an aqueous solution to form dispersed oil and dispersed cationic polymer in an aqueous surfactant solution; and (b) diluting said aqueous surfactant solution such that dispersed cationic polymer particles dissolve and induce formation of cationic polymer/oil aggregates having length greater than 50 micrometers.

* * * * *